US008193193B2

(12) United States Patent
Mizuno et al.

(10) Patent No.: US 8,193,193 B2
(45) Date of Patent: Jun. 5, 2012

(54) AGENT FOR PREVENTION OR TREATMENT OF GLAUCOMA

(75) Inventors: Ken Mizuno, Higashimurayama (JP); Jiro Matsumoto, Sayama (JP)

(73) Assignee: Kowa Co., Ltd., Nagoya-shi (JP)

( * ) Notice: Subject to any disclaimer, the term of this patent is extended or adjusted under 35 U.S.C. 154(b) by 0 days.

(21) Appl. No.: 11/995,052

(22) PCT Filed: Jul. 11, 2006

(86) PCT No.: PCT/JP2006/313740
§ 371 (c)(1),
(2), (4) Date: Jan. 8, 2008

(87) PCT Pub. No.: WO2007/007737
PCT Pub. Date: Jan. 18, 2007

(65) Prior Publication Data
US 2009/0118299 A1    May 7, 2009

(30) Foreign Application Priority Data

Jul. 12, 2005   (JP) .................................. 2005-203352

(51) Int. Cl.
*A61K 31/497* (2006.01)
*A01N 43/62* (2006.01)
(52) U.S. Cl. .................................. 514/253.05; 514/218
(58) Field of Classification Search .................... 514/253
See application file for complete search history.

(56) References Cited

U.S. PATENT DOCUMENTS

| 2,554,816 | A | | 5/1951 | Clapp et al. |
| 4,483,864 | A | * | 11/1984 | Barfknecht et al. .......... 514/363 |
| 4,797,413 | A | | 1/1989 | Baldwin et al. |
| 2005/0059595 | A1 | * | 3/2005 | Lasko et al. .................... 514/12 |
| 2005/0245509 | A1 | | 11/2005 | Nakajima et al. |
| 2006/0052367 | A1 | | 3/2006 | Hatano et al. |
| 2006/0142270 | A1 | * | 6/2006 | Sugimoto et al. ............. 514/218 |
| 2008/0097108 | A1 | * | 4/2008 | Gao et al. .................. 548/359.1 |

FOREIGN PATENT DOCUMENTS

| EP | 1 541 151 A1 | 6/2005 |
| JP | 61-227581 | 10/1986 |
| JP | 2726672 | 12/1997 |
| JP | 11-349482 | 12/1999 |
| JP | 2004-107335 | 4/2004 |
| JP | 2004-182723 | 7/2004 |
| JP | 2004-250410 | 9/2004 |
| WO | WO 91/15486 | 10/1991 |
| WO | WO 99/20620 | 4/1999 |
| WO | WO 00/09162 | 2/2000 |
| WO | WO 01/56988 A1 | 8/2001 |
| WO | WO 01/68607 A1 | 9/2001 |
| WO | WO 02/38158 A1 | 5/2002 |
| WO | WO 03/049745 A1 | 6/2003 |
| WO | WO 03/059913 A1 | 7/2003 |
| WO | WO 03/062227 A1 | 7/2003 |
| WO | WO 03/105724 A2 | 12/2003 |
| WO | 2004 019951 | 3/2004 |
| WO | WO 2004/022541 A1 | 3/2004 |
| WO | WO 2004/039796 A1 | 5/2004 |
| WO | 2004 045644 | 6/2004 |
| WO | WO 2004/084813 A2 | 10/2004 |
| WO | WO 2005/034866 A2 | 4/2005 |
| WO | WO 2005/035501 A1 | 4/2005 |
| WO | WO 2005/035503 A1 | 4/2005 |
| WO | WO 2005/035506 A1 | 4/2005 |
| WO | WO 2005/037197 A2 | 4/2005 |
| WO | WO 2005/037198 A2 | 4/2005 |
| WO | WO 2005/099691 A1 | 10/2005 |

OTHER PUBLICATIONS

Vippagunta et al. (Crystalline Solids, Adv Drug Deliv Rev. May 16, 2001;48(1):3-26).*
Honjo, Megumi et al., "Effects of RHO-Associated Protein Kinase Inhibitor Y-27632 on Intraocular Pressure and Outflow Facility", Investigative Ophthalmology & Visual Science, vol. 42, No. 1, pp. 137 to 144, 2001.
Araie, Makoto et al., "The Efficacy and Safety of Dose Escalation of Dorzolamide Used in Combination With Other Topical Antiglaucoma Agents", Journal of Ocular Pharmacology and Therapeutics, vol. 19, No. 6, pp. 517 to 525, 2003.
Silver, Lewis H., et al., "Clinical Efficacy and Safety of Brinzolamide (Azopt™), A New Topical Carbonic Anhydrase Inhibitor for Primary Open-Angle Glaucoma and Ocular Hypertension" American Journal of Ophthalmology, vol. 126, No. 3, pp. 400 to 408, 1998.
Sugrue, Michael F., et al., "Pharmacological and Ocular Hypotensive Properties of Topical Carbonic Anhydrase Inhibitors", Progress in Retinal and Eye Research, vol. 19, No. 1, pp. 87 to 112, 2000.
B. Becker, "Tropical Carbonic Anhydrase Inhibitor", Journal of the Eye, vol. 15, No. 4, 1998, pp. 481-485 (with partial English translation).
P. Vasantha Rao, et al., Modulation of Aqueous Humor Outflow Facility by the Rho Kinase-Specific Inhibitor Y-27632, Investigative Ophtalmology & Visual Science, vol. 42, No. 5, Apr. 2001, pp. 1029-1037.

(Continued)

*Primary Examiner* — Sreeni Padmanabhan
*Assistant Examiner* — Timothy E Betton
(74) *Attorney, Agent, or Firm* — Oblon, Spivak, McClelland, Maier & Neustadt, L.L.P.

(57) ABSTRACT

There is Provided an Agent for Prevention of glaucoma or an agent for prevention or treatment of ocular hypertension, with a potent ocular hypotensive effect and prolonged duration thereof. An agent for prevention or treatment of glaucoma comprising a Rho kinase inhibitor and a carbonic anhydrase inhibitor in combination.

15 Claims, 1 Drawing Sheet

OTHER PUBLICATIONS

Nobuyuki Negoro, et al., "The Kinase Inhibitor Fasudil (HA-1077) Reduces Intimal Hyperplasia through Inhibiting Migration and Enhancing Cell Loss of Vascular Smooth Muscle Cells", Biochemical and Biophysical Research Communications, vol. 262, 1999, pp. 211-215.

Hideki Tokushige, Bio Clinica, Y-39983, vol. 17, 2002, pp. 1191-1194.

M. Inatani, et al., "Intraocular Pressure-Lowering Effects of Topical Administration of Y-39983, a Novel Selective Rho-Associated Protein Kinase Inhibitor", Association for Research in Vision and Ophthalmology, May 4, 2005, 1 page.

Japanese Office Action issued Sep. 13, 2011, in Patent Application No. 2007-524652 (with English-language translation).

Sachie Maeda et al., "Effect of 1% Brinzolamide on Papillary Circulation in Glaucomatous Eyes", Journal of the Eye (Atarashii Ganka), Apr. 30, 2005, vol. 22, No. 4, pp. 529-532 (with English Abstract).

Extended European Search Report issued Jan. 18, 2012, in Patent Application No. 06780961.6.

* cited by examiner

AGENT FOR PREVENTION OR TREATMENT OF GLAUCOMA

TECHNICAL FIELD

The present invention relates to a preventive or a remedy for glaucoma or ocular hypertension.

BACKGROUND ART

Glaucoma is a disease characterized by the elevation of intraocular pressure (IOP) due to various pathogenesis leads to damage and atrophy of the optic nerve resulting in the abnormal visual field, and thus visual acuity is gradually reduced. Since the optic nerve does not recover once atrophy occurs, glaucoma is a refractory disease in that not only vision is lost if glaucoma is untreated, but also the condition is only maintained even after successful treatment, and recovery cannot be expected. Furthermore, ocular hypertension, which may lead to development of glaucoma over a long time although in the absence of visual field defects, also has a similar risk.

Glaucoma is classified into three types: congenital (developmental) glaucoma, secondary glaucoma, and primary glaucoma. Patients with congenital (developmental) glaucoma are born with growth deficiency of the iridocorneal angle, and obstruction of the aqueous outflow causes this type of glaucoma. Secondary glaucoma arises as a result of inflammation or injury and is caused by such as uveitis or ocular trauma as well as hemorrhage due to diabetes, long-term use of steroid hormones for the treatment of other diseases, and the like. Primary glaucoma is a generic name of glaucomas of types with unclear causes and occurs most commonly of glaucomas, with a high incidence among middle aged and elderly persons. Primary glaucoma and secondary glaucoma are further subdivided into two types, open-angle glaucoma and angle-closure glaucoma, depending on the blockage of the aqueous outflow. While many patients develop normal tension glaucoma in the absence of elevated IOP, the primary aim of glaucoma treatment is to lower the IOP.

For the treatment of glaucoma, laser treatment (laser trabeculoplasty), surgical therapy (trabeculectomy or trabeculotomy), or the like is performed when IOP cannot be controlled with a drug or a patient with angle-closure glaucoma has an acute glaucoma attack, but drug therapy is used as the first line therapy.

Drugs used in the drug therapy of glaucoma include sympathetic nerve stimulants (nonselective stimulants such as epinephrine and $\alpha_2$ stimulants such as apraclonidine), sympathetic nerve blockers ($\beta$ blockers such as timolol, befunolol, carteolol, nipradilol, betaxolol, levobunolol, and metipranolol and $\alpha_1$ blockers such as bunazosin hydrochloride), parasympathetic nerve agonists (pilocarpine, etc.), carbonic anhydrase inhibitors (acetazolamide, etc.), prostaglandins (isopropyl unoprostone, latanoprost, travoprost, bimatoprost, etc.), and so forth.

Of these, carbonic anhydrase inhibitors are known to lower IOP by internal use or instillation thereof because they inhibit the production of aqueous humor in the ciliary body (Non-patent Document 1).

Meanwhile, Rho kinase inhibitors have been found as candidate remedies for glaucoma based on a novel mechanism of action (Patent Documents 1 and 2). Rho kinase inhibitors lower IOP by promoting aqueous outflow from the trabecular outflow pathway (Non-patent Document 2), and it is further suggested that this action may be attributed to changes in the cytoskeleton of a trabecular meshwork cells (Non-patent Documents 2 and 3).

In the treatment of glaucoma and ocular hypertension, drugs having an ocular hypotensive action are used in combination to enhance the ocular hypotensive action. For example, combination use of a prostaglandin and a sympathetic nerve blocker (Patent Document 3), or a combination of some drugs having an ocular hypotensive action (Patent Document 4), and the like have been reported. Furthermore, combination use of a Rho kinase inhibitor and a $\beta$ blocker (Patent Document 5) and a remedy for glaucoma comprising a Rho kinase inhibitor and a prostaglandin in combination (Patent Document 6) have also been reported.

However, the above-mentioned known remedies and therapies for glaucoma and ocular hypertension are far from satisfactory in view of the potency of the ocular hypotensive effect and the duration of action. In particular, it is more difficult to lower normal IOP in patients with normal tension glaucoma rather than lower elevated IOP. The above-mentioned existing drugs and combinations thereof have limitations in the treatment of normal tension glaucoma, and enhancement of the ocular hypotensive action is needed in the clinical setting.

Under such circumstances, there has been no report on glaucoma treatment using a Rho kinase inhibitor and a carbonic anhydrase inhibitor in combination, and there has been no description about the cooperative effect of such a combination.

[Patent Document 1] WO00/09162
[Patent Document 2] JP-A-11-349482
[Patent Document 3] Japanese Patent No. 2726672
[Patent Document 4] WO02/38158
[Patent Document 5] JP-A-2004-182723
[Patent Document 6] JP-A-2004-107335
[Non-patent Document 1] Journal of the Eye, 15(4), 481-485 (1998)
[Non-patent Document 2] IOVS, 42(1), 137-144 (2001)
[Non-patent Document 3] IOVS, 42(5), 1029-1037 (2001)

DISCLOSURE OF THE INVENTION

An object of the present invention is to provide a preventive or a remedy for glaucoma or ocular hypertension with a potent ocular hypotensive effect and a prolonged duration of action.

The inventors of the present invention conducted various researches in order to achieve the foregoing object. As a result, we have found that a potent ocular hypotensive effect is exerted by administering a Rho kinase inhibitor and a carbonic anhydrase inhibitor in combination, and the duration of action is prolonged.

Specifically, the present invention relates to the followings.
1) A preventive or a remedy for glaucoma comprising a Rho kinase inhibitor and a carbonic anhydrase inhibitor in combination.
2) A preventive or a remedy for ocular hypertension comprising a Rho kinase inhibitor and a carbonic anhydrase inhibitor in combination.
3) Use of a Rho kinase inhibitor and a carbonic anhydrase inhibitor in combination for production of a preventive or a remedy for glaucoma.
4) Use of a Rho kinase inhibitor and a carbonic anhydrase inhibitor in combination for production of a preventive or a remedy for ocular hypertension.

5) A method for preventing or treating glaucoma, wherein the method comprises administrating a Rho kinase inhibitor and a carbonic anhydrase inhibitor in combination.

6) A method for preventing or treating ocular hypertension, wherein the method comprises administrating a Rho kinase inhibitor and a carbonic anhydrase inhibitor in combination.

According to the present invention, a preventive or a remedy for glaucoma or ocular hypertension with a potent ocular hypotensive effect and a prolonged duration of action can be provided.

BEST MODE FOR CARRYING OUT THE INVENTION

Figure 1:
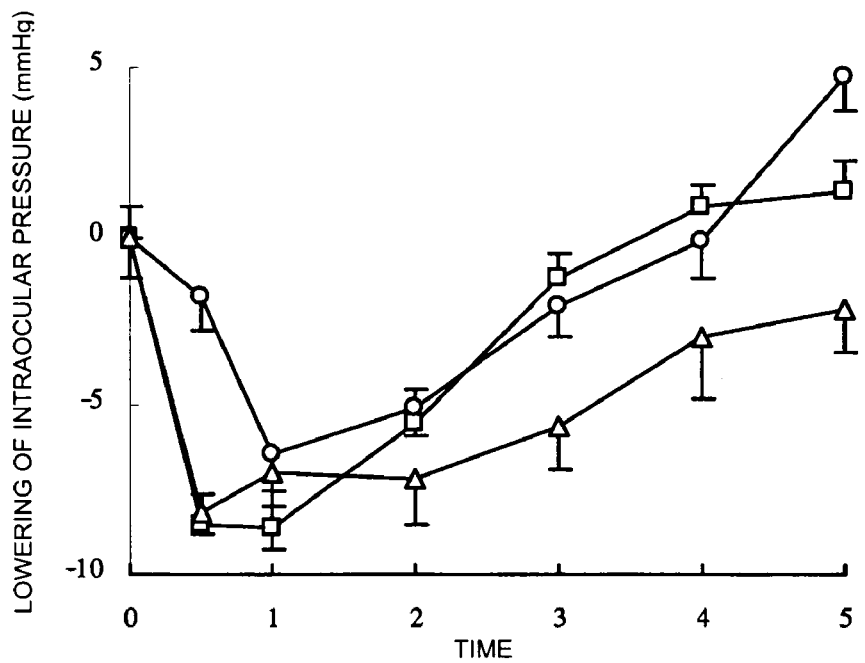
FIG. 1 is a graph showing changes in IOP over time in each treatment group. IOP is shown as a change from the initial IOP (mean±standard error). ○, brinzolamide alone group; □, (S)-(−)-1-(4-fluoro-5-isoquinolinesulfonyl)-2-methyl-1,4-homopiperazine alone group; Δ, brinzolamide plus (S-(−)-1-(4-fluoro-5-isoquinolinesulfonyl)-2-methyl-1,4-homopiperazine group.

In the present invention, "Rho kinase inhibitor" refers to a substance that inhibits Rho kinase, an enzyme phosphorylating "Rho" known as one of low molecular weight GTP binding proteins.

Examples of such Rho kinase inhibitors include isoquinoline derivatives described in JP-A-11-349482 (the abovementioned Patent Document 2), compounds described in WO05/37198, WO05/37197, WO05/35501, WO05/35506, WO05/35503, WO05/34866, WO04/84813, JP-A-2004-250410, WO04/39796, WO04/22541, WO03/59913, WO03/62227, WO01/68607, and WO01/56988, (S)-(−)-1-(4-fluoro-5-isoquinolinesulfonyl)-2-methyl-1,4-homopiperazine (WO99/20620), hexahydro-1-(5-isoquinolinesulfonyl)-1H-1,4-diazepine (Biochem. Biophys. Res. Commun. 262(1), 211-215 (1999)), Y-39983 (4-[(1R)-1-aminoethyl]-N-1H-pyrrolo[2,3-b]pyridin-4-ylbenzamide) (BIO Clinica, 17[13], 1191-1194 [2002]; The 4th Int. Symp. Ocular Pharmacol. Pharm. [Feb. 28, 2002, Seville] 2002: 2; Annu. Meet. Assoc. Res. Vision Ophthalmol. [May 1, 2005, Fort Lauderdale] 2005: Abst. 3787/B145), and so forth.

Of these, (S)-(−)-1-(4-fluoro-5-isoquinolinesulfonyl)-2-methyl-1,4-homopiperazine or salts thereof, hexahydro-1-(5-isoquinolinesulfonyl)-1H-1,4-diazepine or salts thereof, and Y-39983 are more preferred, and salts of (S)-(−)-1-(4-fluoro-5-isoquinolinesulfonyl)-2-methyl-1,4-homopiperazine are particularly preferred.

(S)-(−)-1-(4-fluoro-5-isoquinolinesulfonyl)-2-methyl-1, 4-homopiperazine is a compound having antagonistic actions against substance P and leukotriene D4 in addition to a Rho kinase inhibiting action and can be produced by known methods such as, for example, the method described in WO99/20620.

Hexahydro-1-(5-isoquinolinesulfonyl)-1H-1,4-diazepine can be produced by known methods such as, for example, the method described in JP-A-61-227581 and, further, can be purchased and used as a drug (Eril® S Injection [nonproprietary name: fasudil hydrochloride hydrate], Asahi Kasei Pharma).

Furthermore, Y-39983 is known to lower IOP in rabbits with normal IOP from 1 hour after instillation, shows the maximum ocular hypotensive effect at 2 to 4 hours after instillation, and has a potent action dependent on the concentration, with the maximum IOP reduction of 15 mmHg at a concentration of 0.1% (BIO Clinica, 17[13], 1191-1194 [2002]; The 4th Int. Symp. Ocular Pharmacol. Pharm. [Feb. 28, 2002, Seville] 2002: 2; Annu. Meet. Assoc. Res. Vision Opthalmol. [May 1, 2005, Fort Lauderdale] 2005: Abst. 3787/B145).

Examples of salts of (S)-(−)-1-(4-fluoro-5-isoquinolinesulfonyl)-2-methyl-1,4-homopiperazine and hexahydro-1-(5-isoquinolinesulfonyl)-1H-1,4-diazepine include pharmaceutically acceptable salts such as salts of inorganic acids such as hydrochloric acid, sulfuric acid, nitric acid, hydrofluoric acid, and hydrobromic acid and salts of organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphorsulfonic acid, and hydrochlorides are particularly preferred.

(S)-(−)-1-(4-fluoro-5-isoquinolinesulfonyl)-2-methyl-1, 4-homopiperazine and hexahydro-1-(5-isoquinolinesulfonyl)-1H-1,4-diazepine or salts thereof can exist not only as unsolvated forms, but also as hydrates or solvates, and the present invention includes all the crystalline forms of these compounds and hydrates or solvates thereof.

In the present invention, "carbonic anhydrase inhibitor" refers to an agent that inhibits a carbonic anhydrase, which catalyzes the reversible reactions of hydration of $CO_2$ and dehydration of carbonic acid ($CO_2+H_2O \leftrightarrows H_2CO_3$). Carbonic anhydrase is known to have multiple isoenzymes such as types I and II, and selective inhibitors of type-II carbonic anhydrase are preferred as the carbonic anhydrase inhibitor used in the present invention.

Examples of such carbonic anhydrase inhibitors include brinzolamide, dorzolamide hydrochloride, acetazolamide, methazolamide, and so forth. Of these, brinzolamide is preferred.

These carbonic anhydrase inhibitors are known to lower IOP by selectively inhibiting type-II carbonic anhydrases with the highest activity in the ciliary body (Prog. Retin. Eye Res. 2000 January; 19(1): 87-112) and thereby suppressing secretion of aqueous humor (Am. J. Opthalmol. 1998 September; 126(3): 400-408) and can be produced by known methods such as, for example, the methods described in WO91/15486, U.S. Pat. Nos. 4,797,413 and 2,554,816, and the like. Furthermore, a remedy for glaucoma and ocular hypertension such as "AZOPT® Ophthalmic Suspension 1%" (Alcon Japan Ltd.), "Trusopt® Ophthalmic Solution 1%" (Banyu Pharmaceutical Co., Ltd.), or the like can be used as ophthalmic preparations.

When a Rho kinase inhibitor and a carbonic anhydrase inhibitor are used in combination, a potent and prolonged ocular hypotensive effect is exhibited even from normal IOP as shown in the examples described later. Therefore, a medicament containing these compounds is useful as a preventive or a remedy for glaucoma or ocular hypertension. Here, examples of glaucomas include primary open-angle glaucoma, normal tension glaucoma, glaucoma with excessive hypersecretory form, ocular hypertension, acute angle-closure glaucoma, chronic angle-closure glaucoma, plateau iris syndrome, combined-mechanism glaucoma, steroid glaucoma, pseudoexfoliation glaucoma, pigmentary glaucoma, amyloid glaucoma, neovascularization glaucoma, malignant glaucoma, and so forth. Furthermore, ocular hypertension is also called "high blood pressure of the eye" and refers to a symptom with abnormally high IOP even in the absence of any clear lesion in the optic nerve. Many high IOP conditions such as postoperative high IOP fall within the scope of the present invention.

The preventive or the remedy for glaucoma or ocular hypertension comprising a Rho kinase inhibitor and a carbonic anhydrase inhibitor in combination of the present invention may be prepared in one dosage form comprising effective amounts of the respective drugs at a suitable mixing ratio as a combination drug or a kit used by administering preparations each comprising an effective amount of drug either simultaneously or separately at an interval.

The above-mentioned preparations may be either parenteral or oral preparations and can be prepared in the forms of, for example, opthalmological preparation, injection, tablet, capsule, powder, granule, solution, and the like. These preparations can be prepared by known techniques by suitably adding known carriers. It is preferably used, among others, as an opthalmological preparation, particularly preferably as an instillation, and such an ophthalmic preparation may be aqueous eye drop, nonaqueous eye drop, suspension eye drop, emulsion eye drop, eye ointment, and the like. The preparation can be produced by preparation methods known to those skilled in the art as a composition suitable for the dosage form by adding pharmacologically acceptable carriers such as, for example, tonicity agents, chelating agents, stabilizers, pH modifiers, preservatives, antioxidants, solubilizing agents, and thickening agents, if necessary.

Examples of tonicity agents include saccharides such as glucose, trehalose, lactose, fructose, mannitol, xylitol, and sorbitol, polyhydric alcohols such as glycerine, polyethylene glycol, and propylene glycol, inorganic salts such as sodium chloride, potassium chloride, and calcium chloride, and so forth, and the addition amount thereof is preferably 0 to 5% by weight based on the total amount of the composition.

Examples of chelating agents include edetates such as disodium edetate, calcium disodium edetate, trisodium edetate, tetrasodium edetate, and calcium edetate, ethylenediamine tetraacetate, nitrilotriacetic acid or salts thereof, sodium hexametaphosphate, citric acid, and so forth, and the blending quantity thereof is preferably 0 to 0.2% by weight based on the total amount of the composition.

Examples of stabilizers include sodium hydrogen sulfite and so forth, and the blending quantity thereof is preferably 0 to 1% by weight based on the total amount of the composition.

Examples of pH modifiers include acids such as hydrochloric acid, carbonic acid, acetic acid, citric acid, phosphoric acid, and boric acid, further alkali metal hydroxides such as sodium hydroxide and potassium hydroxide, alkali metal carbonates such as sodium carbonate or hydrogen carbonates, alkali metal acetates such as sodium acetate, alkali metal citrates such as sodium citrate, bases such as trometamol, and so forth, and the blending quantity thereof is preferably 0 to 20% by weight based on the total amount of the composition.

Examples of preservatives include sorbic acid, potassium sorbate, parahydroxybenzoate esters such as methyl parahydroxybenzoate, ethyl parahydroxybenzoate, propyl parahydroxybenzoate, and butyl parahydroxybenzoate, chlorhexidine gluconate, quaternary ammonium salts such as benzalkonium chloride, benzethonium chloride, and cetylpyridinium chloride, alkylpolyaminoethylglycine, chlorobutanol, Polyquad, polyhexamethylene biguanide, chlorhexidine, and so forth, and the blending quantity thereof is preferably 0 to 0.2% by weight based on the total amount of the composition.

Examples of antioxidants include sodium hydrogen sulfite, dry sodium sulfite, sodium pyrosulfite, concentrated mixed tocopherol, and so forth, and the blending quantity thereof is preferably 0 to 0.4% by weight based on the total amount of the composition.

Examples of solubilizing agents include sodium benzoate, glycerine, D-sorbitol, glucose, propylene glycol, hydroxypropylmethylcellulose, polyvinylpyrrolidone, macrogol, D-mannitol, and so forth, and the blending quantity thereof is preferably 0 to 3% by weight based on the total amount of the composition.

Examples of thickening agents include polyethylene glycol, methylcellulose, ethylcellulose, carmellose sodium, xanthan gum, sodium chondroitin sulfate, hydroxyethylcellulose, hydroxypropylcellulose, hydroxypropylmethylcellulose, polyvinylpyrrolidone, polyvinyl alcohol, and so forth, and the blending quantity thereof is preferably 0 to 70% by weight based on the total amount of the composition.

An ophthalmic preparation can be prepared by, for example, dissolving or suspending desired ingredients of the above-mentioned compounds in an aqueous solvent such as sterilized purified water or physiological saline or a nonaqueous solvent such as vegetable oil such as cottonseed oil, soybean oil, sesame oil, or peanut oil at a predetermined osmotic pressure and subjecting the solution or suspension to sterilization such as sterilization by filtration. When an eye ointment is prepared, an ointment base can be added in addition to the above-mentioned various ingredients. The above-mentioned ointment base is not particularly limited, but preferred examples thereof include oily bases such as Vaseline, liquid paraffin, and polyethylene, emulsion bases obtained by emulsifying the oil phase and the aqueous phase with a surfactant or the like, water-soluble bases comprising hydroxypropylmethylcellulose, carboxymethylcellulose, polyethylene glycol or the like, and so forth.

When the preventive or the remedy for glaucoma or ocular hypertension of the present invention is provided as a kit, it can be designed so that drugs each comprising a Rho kinase inhibitor or a carbonic anhydrase inhibitor prepared as described above should be separately packaged, and each drug preparation is removed from each package before use. Furthermore, both the drug preparations can be packaged in a form suitable for combination use for each dose.

The dose of the agent for prevention or treatment of glaucoma or ocular hypertension of the present invention varies depending on the patient's body weight, age, sex, symptom, dose form, number of dosages, and the like, but the usual adult daily dose of a Rho kinase inhibitor is in the range of 0.025 to 2000 µg, preferably 0.1 to 1000 µg in an ophthalmic solution, or 0.1 to 1000 mg in an oral preparation or an injection. The usual adult daily dose of a carbonic anhydrase inhibitor is in the range of 10 to 2000 µg, preferably 50 to 1000 µg in an ophthalmic solution, or 1 to 1500 mg in an oral preparation or an injection.

The number of dosages is not particularly limited, but it is preferable to administer the dose once daily or divide the dose into several times. One to several drops of a liquid eye drop can be instilled as one dose. An oral preparation or an injection can be administered once to several times daily.

When the preparations are packaged as a kit, the individual preparations may be administered simultaneously or at an interval of 5 minutes to 24 hours.

The present invention will be explained more specifically with reference to the following examples. However, the scope of the present invention is not limited to these examples.

EXAMPLES

Example 1

Figure 2:
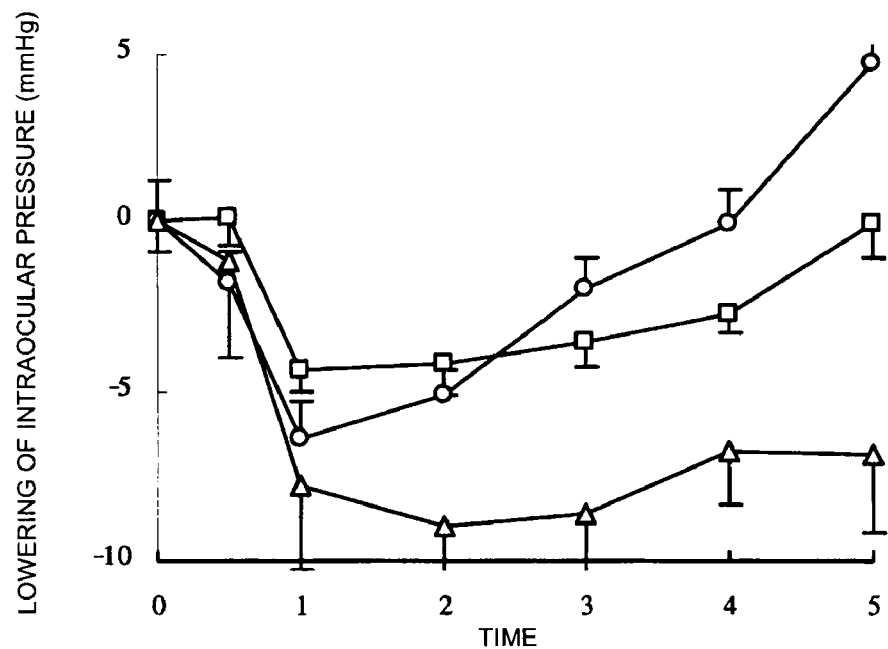
FIG. 2 is a graph showing changes in IOP over time in each treatment group. IOP is shown as a change from the initial IOP (mean±standard error). ○, brinzolamide alone group; □, hexahydro-1-(5-isoquinolinesulfonyl)-1H-1,4-diazepine alone group; Δ, brinzolamide plus hexahydro-1-(5-isoquinolinesulfonyl)-1H-1,4-diazepine group.

To examine usefulness of combination use of a Rho kinase inhibitor and a carbonic anhydrase inhibitor, the ocular hypotensive effects were compared by administering either of these drugs alone or both in combination to laboratory animals.
1. Preparation of Test Compound Solutions
A. Preparation of (S)-(−)-1-(4-fluoro-5-isoquinolinesulfonyl)-2-methyl-1,4-homopiperazine Solution
(S)-(−)-1-(4-fluoro-5-isoquinolinesulfonyl)-2-methyl-1,4-homopiperazine-hydrochloride dihydrate was dissolved in physiological saline, and the solution was neutralized (pH 6.0) by adding sodium dihydrogenphosphate and sodium hydroxide to prepare a (S)-(−)-1-(4-fluoro-5-isoquinolinesulfonyl)-2-methyl-1,4-homopiperazine solution at a desired concentration.
B. Preparation of hexahydro-1-(5-isoquinolinesulfonyl)-1H-1,4-diazepine Solution
The commercially available "Eril® S Injection" (Asahi Kasei Pharma) was used as it was.
C. Preparation of Brinzolamide Solution
The commercially available "Azopt® Ophthalmic Suspension 1%" (Alcon Japan Ltd.) was used as it was.
2. Test Method
The ocular hypotensive effect was examined after the combination use of (S)-(−)-1-(4-fluoro-5-isoquinolinesulfonyl)-2-methyl-1,4-homopiperazine and brinzolamide. As a control, the ocular hypotensive effect was also examined after the use of brinzolamide alone or (S)-(−)-1-(4-fluoro-5-isoquinolinesulfonyl)-2-methyl-1,4-homopiperazine alone.
Similarly, the ocular hypotensive effect was examined after the combination use of hexahydro-1-(5-isoquinolinesulfonyl)-1H-1,4-diazepine and brinzolamide. As a control, the ocular hypotensive effect was also examined after the use of brinzolamide alone or hexahydro-1-(5-isoquinolinesulfonyl)-1H-1,4-diazepine alone.
A. Drugs and Animals Used in Test
(S)-(−)-1-(4-fluoro-5-isoquinolinesulfonyl)-2-methyl-1,4-homopiperazine solution: 0.5% solution (instillation volume, 50 μL)
Hexahydro-1-(5-isoquinolinesulfonyl)-1H-1,4-diazepine solution: fasudil hydrochloride hydrate injection (1.5% solution [trade name: Eril® S Injection]; instillation volume, 50 μL)
Brinzolamide solution: brinzolamide ophthalmic solution ([trade name: Azopt® Ophthalmic Suspension 1%]; instillation volume, 50 μL)
Laboratory animals: Japanese white rabbits (male JW rabbits, 5 animals per group)
B. Administration and Measurement
(1) Administration of Two Drugs in Combination
1). One drop of 0.4% oxybuprocaine hydrochloride ophthalmic solution (trade name: Benoxil Ophthalmic Solution 0.4%) was instilled in both eyes of the laboratory animals for local anesthesia (only data for the instilled eyes are shown).
2) IOP was measured immediately before administration of the test compound solution as the initial IOP.
3) The brinzolamide solution was instilled in one eye of the laboratory animals, followed by the instillation of (S)-(−)-1-(4-fluoro-5-isoquinolinesulfonyl)-2-methyl-1,4-homopiperazine solution in the same eye.
4) At 1 hour, 2 hours, 3 hours, 4 hours, and 5 hours after the instillation of both drugs, one drop each of 0.4% oxybuprocaine hydrochloride ophthalmic solution was instilled in both eyes for local anesthesia, and IOP was measured.
(2) Administration of Single Drug Alone
The (S)-(−)-1-(4-fluoro-5-isoquinolinesulfonyl)-2-methyl-1,4-homopiperazine solution alone or the brinzolamide solution alone was instilled, and then tests were performed at the same measurement timings as in the above-described combination use test.
The hexahydro-1-(5-isoquinolinesulfonyl)-1H-1,4-diazepine solution and the brinzolamide solution were administered in combination or either of them alone in the same manner as in the above (1) and (2).
3. Results and Discussion
The test results are shown in FIGS. 1 and 2. IOP are shown as changes (mean±standard error) from the initial IOP.
As shown in FIG. 1, a superior ocular hypotensive effect was observed in the (S)-(−)-1-(4-fluoro-5-isoquinolinesulfonyl)-2-methyl-1,4-homopiperazine plus brinzolamide group to those in the single drug treatment groups, i.e., the (S)-(−)-1-(4-fluoro-5-isoquinolinesulfonyl)-2-methyl-1,4-homopiperazine alone group and the brinzolamide alone group. Furthermore, the action remained in the combination treatment group even after 3 or 4 hours, when the ocular hypotensive effect disappeared in the single drug treatment groups, showing improvement of the prolonged action.
Similarly in FIG. 2, a superior ocular hypotensive effect was observed in the hexahydro-1-(5-isoquinolinesulfonyl)-1H-1,4-diazepine plus brinzolamide group than in the single drug treatment groups, i.e., the hexahydro-1-(5-isoquinolinesulfonyl)-1H-1,4-diazepine alone group and the brinzolamide alone group. Furthermore, since the action remained in the combination treatment group even after 4 and also 5 hours, when the ocular hypotensive effect disappeared in the single drug treatment groups, showing improvement of prolongation of the action.
The above results revealed that a potent ocular hypotensive effect and improvement of the prolonged action could be obtained by using brinzolamide and (S)-(−)-1-(4-fluoro-5-isoquinolinesulfonyl)-2-methyl-1,4-homopiperazine or hexahydro-1-(5-isoquinolinesulfonyl)-1H-1,4-diazepine in combination.

The invention claimed is:
1. A composition, comprising
   a Rho kinase inhibitor, or a salt thereof, wherein said Rho kinase inhibitor is selected from the group consisting of (S)-(−)-1-(4-fluoro-5-isoquinolinesulfonyl)-2-methyl-1,4-homopiperazine, and hexahydro-1-(5-isoquinolinesulfonyl)-1H-1,4-diazepine, and
   brinzolamide or a salt thereof.
2. The composition of claim 1, wherein the Rho kinase inhibitor is (S)-(−)-1-(4-fluoro-5-isoquinolinesulfonyl)-2-methyl-1,4-homopiperazine or a salt thereof.
3. The composition of claim 1, which is a combination drug.
4. A kit, comprising
   a first drug comprising a Rho kinase inhibitor, or a salt thereof, wherein said Rho kinase inhibitor is selected from the group consisting of (S)-(−)-1-(4-fluoro-5-isoquinolinesulfonyl)-2-methyl-1,4-homopiperazine, and hexahydro-1-(5-isoquinolinesulfonyl)-1H-1,4-diazepine, and
   a second drug comprising brinzolamide or a salt thereof.

5. A method of treating ocular hypertension in an eye, the method comprising
administering a Rho kinase inhibitor or a salt thereof, wherein said Rho kinase inhibitor is selected from the group consisting of (S)-(−)-1-(4-fluoro-5-isoquinolinesulfonyl)-2-methyl-1,4-homopiperazine, and hexahydro-1-(5-isoquinolinesulfonyl)-1H-1,4-diazepine, and brinzolamide or a salt thereof, to the eye in amounts sufficient to treat the ocular hypertension.

6. A method of treating glaucoma in an eye, the method comprising
administrating a Rho kinase inhibitor, or a salt thereof, wherein said Rho kinase inhibitor is selected from the group consisting of (S)-(−)-1-(4-fluoro-5-isoquinolinesulfonyl)-2-methyl-1,4-homopiperazine, and hexahydro-1-(5-isoquinolinesulfonyl)-1H-1,4-diazepine, and brinzolamide or a salt thereof, to the eye in amounts sufficient to treat the glaucoma.

7. The method of claim 6, wherein the glaucoma is selected from primary open-angle glaucoma, normal tension glaucoma, glaucoma with excessive hypersecretory form, acute angle-closure glaucoma, chronic angle-closure glaucoma, combined-mechanism glaucoma, steroid glaucoma, pseudoexfoliation glaucoma, pigmentary glaucoma, amyloid glaucoma, neovascularization glaucoma, malignant glaucoma, Plateau iris syndrome, and combinations thereof.

8. The method of claim 5, wherein the Rho kinase inhibitor or the salt thereof, and brinzolamide or the salt thereof, are administered as separate formulations.

9. The method of claim 8, wherein the separate formulations are administered separately at an interval.

10. The method of claim 9, wherein at least one of the formulations is an aqueous solution or suspension.

11. The method of claim 6, wherein the Rho kinase inhibitor or the salt thereof and brinzolamide or the salt thereof, are administered as separate formulations.

12. The method of claim 11, wherein the separate formulations are administered separately at an interval.

13. The method of claim 12, wherein at least one of the formulations is an aqueous solution or suspension.

14. The method of claim 13, comprising the salt of the Rho kinase inhibitor,
wherein the salt of the Rho kinase inhibitor is (S)-(−)-1-(4-fluoro-5-isoquinolinesulfonyl)-2-methyl-1,4-homopiperazine-hydrogen chloride dihydrate, and
wherein the formulation comprising the (S)-(−)-1-(4-fluoro-5-isoquinolinesulfonyl)-2-methyl-1,4-homopiperazine-hydrogen chloride dihydrate is an aqueous solution.

15. The method claim 10, comprising the salt of the Rho kinase inhibitor,
wherein the salt of the Rho kinase inhibitor is (S)-(−)-1-(4-fluoro-5-isoquinolinesulfonyl)-2-methyl-1,4-homopiperazine-hydrogen chloride dihydrate, and
wherein the formulation comprising the (S)-(−)-1-(4-fluoro-5-isoquinolinesulfonyl)-2-methyl-1,4-homopiperazine-hydrogen chloride dihydrate is an aqueous solution.

* * * * *